United States Patent [19]

Lüning

[11] 4,327,075
[45] Apr. 27, 1982

[54] SYNTHETIC ANTIGENICALLY-ACTIVE POLYPEPTIDE AND A PROCESS FOR ITS PREPARATION

[75] Inventor: Björn Lüning, Stockholm, Sweden

[73] Assignee: AB Bonnierföretagen, Stockholm, Sweden

[21] Appl. No.: 139,887

[22] Filed: Apr. 14, 1980

[30] Foreign Application Priority Data

Apr. 20, 1979 [SE] Sweden ............................ 7903505

[51] Int. Cl.$^3$ .................... A61K 39/00; A61K 37/00; C07C 103/52; C01N 31/00
[52] U.S. Cl. ........................................ 424/12; 424/177; 424/88; 260/112.5 R; 23/230 B; 252/408
[58] Field of Search ............... 260/112.5 R; 424/177, 424/12, 88; 23/230 D; 252/408 R

[56] References Cited

U.S. PATENT DOCUMENTS

| | | | |
|---|---|---|---|
| 3,485,810 | 12/1969 | Tilak | 260/112.5 R |
| 3,912,711 | 10/1975 | Leeman et al. | 260/112.5 R |
| 3,915,949 | 10/1975 | Colescott et al. | 260/112.5 R |
| 3,926,938 | 12/1975 | Hughes et al. | 260/112.5 R |
| 3,960,827 | 6/1976 | Björklund | 424/177 |
| 4,028,315 | 6/1977 | Bodanszky et al. | 260/112.5 R |
| 4,031,070 | 6/1977 | Tinney | 260/112.5 R |
| 4,033,940 | 7/1977 | Hughes et al. | 260/112.5 R |
| 4,062,746 | 12/1977 | Rich et al. | 260/112.5 R |
| 4,062,815 | 12/1977 | Hughes et al. | 260/112.5 R |
| 4,160,018 | 7/1979 | Björklund | 260/112.5 R |
| 4,160,019 | 7/1979 | Björklund | 260/112.5 R |
| 4,174,385 | 11/1979 | Reid | 260/112.5 R |

OTHER PUBLICATIONS

Lüning et al., Chem. Abstrs., vol. 87, 1977, 165843m, 116227e, 82872u.

*Primary Examiner*—Delbert R. Phillips
*Attorney, Agent, or Firm*—Gordon W. Hueschen

[57] ABSTRACT

A synthetic antigenically active polypeptide, which includes the amino acid sequence:H-Asp-Ala-Glu-Gln-Arg-Gly-Glu-Leu-Ala-Ile-Arg-Asp-Ala-Asn-Ala-Arg-Leu-Ser-Glu-Leu-OH; a process for the preparation of such polypeptide; an antigenic agent comprising such polypeptide convalently bonded to an immunogenically active carrier; a pharmaceutical composition comprising such polypeptide or antigenic agent together with a pharmaceutically acceptable carrier or diluent; and a method for determining the presence or absence in a biological sample of antibodies monospecific to such polypeptide, which comprises introducing into the sample such polypeptide or such agent or such composition and determining the presence or absence of agglutination.

8 Claims, No Drawings

SYNTHETIC ANTIGENICALLY-ACTIVE POLYPEPTIDE AND A PROCESS FOR ITS PREPARATION

TECHNICAL FIELD

The present invention relates to a synthetic antigenically active polypeptide which includes certain aminoacid sequences, and a process for the preparation of said polypeptide.

BACKGROUND ART

In published Swedish patent application 73- 08917-9 and in U.S. Pat. No. 3,960,827 there is described a cancer-associated polypeptide antigen (CAPA), the technique for its isolation and its use in cancer diagnosis and in the preparation of antibodies. The CAPA is now commercialized under the designation TPA, which stands for "tissue polypeptide antigen". As is clear from the specification of the above-identified Swedish patent application and U.S. patent, the isolation of the natural antigen is a complicated procedure which, even if resulting in a practically useful product, still involves high production costs and moreover may involve difficulties in the provision of necessary starting materials, such as tumor tissue, etc. Against this background a synthetically prepared antigen would, of course, by very attractive, in view of the possibility of thereby obtaining a product exactly specified as to its composition, said product also being capable of being prepared at a more favorable price.

SUMMARY OF THE INVENTION

The main object of this invention is thus to provide a synthetic antigenically active polypeptide which reacts monospecifically with antibodies prepared by means of the polypeptide antigen described in the above-identified patent specifications.

According to this invention there is thus provided a synthetic antigenically active polypeptide including the amino acid sequence:
H-Asp-Ala-Glu-Gln-Arg-Gly-Glu-Leu-Ala-Ile-Arg-Asp-Ala-Asn-Ala-Arg-Leu-Ser-Glu-Leu-OH.

According to one preferred embodiment of the instant invention, there is provided a synthetic antigenically active polypeptide containing as an active constituent or immunological determinative group the amino acid sequence: (I) H-Asp-Ala-Glu-Gln-Arg-Gly-Glu-Leu-Ala-Ile-Arg-Asp-Ala-Asn-Ala-Arg-Leu-Ser-Glu-Leu-Glu-Ala-Ala-Leu-Gln-Arg-Ala-Lys-Gln-Asp-OH.

According to another preferred embodiment of the instant invention, the polypeptide contains the amino acid sequence: (II) H-Ala-Ser-Leu-Glu-Ala-Ala-Ile-Ala-Asp-Ala-Glu-Gln-Arg-Gly-Glu-Leu-Ala-Ile-Arg-Asp-Ala-Asn-Ala-Arg-Leu-Ser-Glu-Leu-OH.

From hereon the following abbreviations for the amino acids in question are used:

| ALANINE | Ala | SERINE | Ser |
|---|---|---|---|
| ARGININE | Arg | LEUCINE | Leu |
| ASPARAGINE | Asn | TYROSINE | Tyr |
| ASPARTIC ACID | Asp | VALINE | Val |
| GLUTAMINE | Gln | THREONINE | Thr |
| GLUTAMIC ACID | Glu | PHENYLALANINE | Phe |
| GLYCINE | Gly | LYSINE | Lys |
| ISOLEUCINE | Ile | | |

The present invention also relates to a process for the preparation of the antigenically active polypeptide, and in this process an N-protected amino acid is attached to a resin by esterification, the N-protecting group is removed and a second N-protected amino acid is coupled to the amino group of the resin-bound amino acid, the N-protecting group is removed and the coupling step is repeated with a third N-protected amino acid. Protecting groups in the process are the usual groups, and are set forth more fully in the following. This procedure is repeated until the desired amino acid sequence is obtained, the polypeptide being then cleaved from the resin. It is preferred after each attachment of an N-protected amino acid to the resin-bound amino acid to wash away all by-products and unreacted soluble materials.

The resin used in the synthesis may consist of a copolymer of styrene and divinyl benzene, the styrene constituting the major part of the copolymer, for instance about 98% by weight of styrene and about 2% by weight of divinyl benzene.

In order to provide a reactive group for coupling to the first amino acid, the benzene rings are suitably partially chloromethylated. When this chloromethylated resin is treated with the triethylamine salt of an N-protected amino acid, a bond of the benzyl ester type is formed. Such bond is stable under the synthesis steps, but can be cleaved with HBr in acetic acid or trifluoroacetic acid, the N-protecting group being simultaneously removed and the peptide separated from the resin.

In order to protect the N-terminus of amino acid the t-butyloxycarbonyl group can suitably be used as it is conveniently cleaved by means of HCl in acetic acid. It is also possible to use the carbobenzoxy group for the purpose, but in this case HBr in acetic acid must be used for removal of the protecting group. As a protecting group there may also be used the o-nitrophenyl sulfenyl group. Other protecting groups may also be employed and will be apparent to one skilled in the art.

The coupling reagent most frequently used in the synthesis is dicyclohexylcarbodiimide. If methylene chloride is used as a solvent and about 50% excess of t-butyloxy carbonyl aminoacid and dicyclohexyl carbodiimide, a quantitative reaction is obtained within a few minutes. Even dimethylformamide may be used as a solvent. Further details regarding the synthesis procedure may be found in "Protein Sequence Determination" summarized by Saul. B. Needleman, Springer-Verlag, Berlin-Heidelberg-New York, 1970, particularly at pp. 308–310. Other coupling agents are also suitable and will be apparent to one skilled in this art.

EXAMPLES

The present invention will now be illustrated further by means of non-limiting examples.

EXAMPLE 1

By the process in solid phase according to Merrifield (cf. the above literature reference) the following product is prepared:

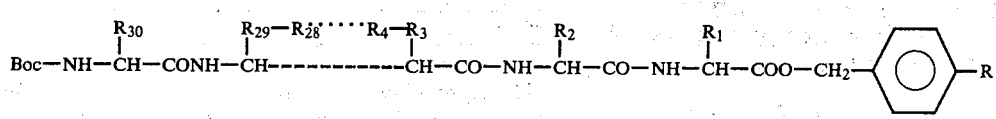

wherein: R denotes a resin; Boc is a t-butyloxy carbonyl group;

Ser-Glu-Leu-Glu-Ala-Ala-Leu-Gln-Arg-Ala-Lys-Gln-Asp-.

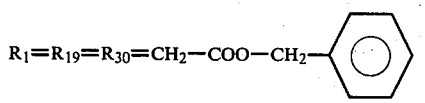

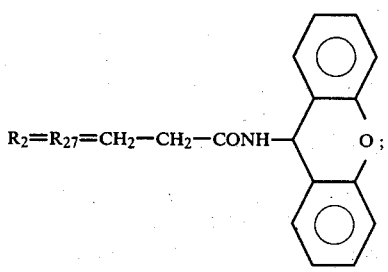

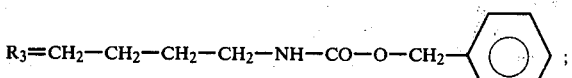

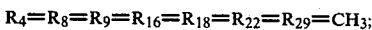

$R_4=R_8=R_9=R_{16}=R_{18}=R_{22}=R_{29}=CH_3$;

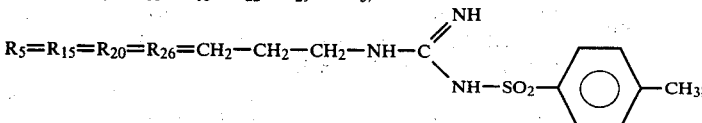

$R_6=R_2=R_{27}$;

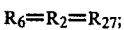

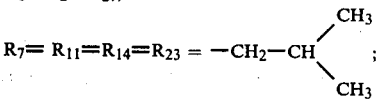

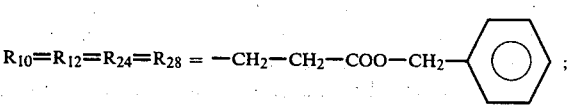

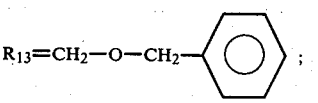

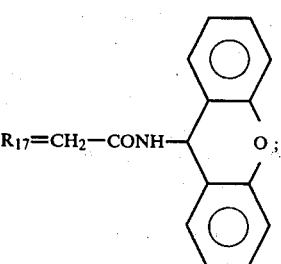

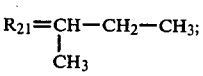

$R_{25}=H$;

The amino acid sequence between the t-butyl-oxycarbonyl group and the resin part may be expressed in the following manner using the foregoing abbreviations regarding the amino acids: (I)-Asp-Ala-Glu-Gln-Arg-Gly-Glu-Leu-Ala-Ile-Arg-Asp-Ala-Asn-Ala-Arg-Leu- 0.4 mmole of Boc-aspartic acid β-benzyl ester α-(resinbenzyl ester) was transferred to the cuvette of a Beckman peptide synthesizer and swollen in methylene chloride (CH₂Cl₂). The protecting Boc-group was removed by treatment with trifluoroacetic acid in excess in methylene chloride. After washing with methylene chloride the resin was neutralized with triethylamine and again washed with methylene chloride. N-Boc-glutamic acid benzyl ester (coupling step 1) and cyclohexylcarbodiimide was added dissolved in $CH_2Cl_2$, and the mixture was stirred for 30 minutes. The resin was washed and the coupling step repeated. This terminates the introduction of $R_2$ in step 1 according to the above.

Step 2 of the synthesis starts by removal of an N-Boc from the N-terminated amino acid and repetition of the coupling step while using another N-Boc-amino acid. To build up the above amino acid sequence the following reagents are used in the subsequent steps: in step 2: N-Boc-glutamine-xanthydryl derivative
3: $\alpha$N-Boc-$\epsilon$(o-chloro-carbobenzoxy)lysine
4: N-Boc-alanine
5: N-Boc-G-tosyl arginine
6: As in step 2
7: N-Boc-leucine
8: As in step 4
9: As in step 4
10: N-Boc-glutamic acid $\gamma$-benzyl ester
11: As in step 7.
12: As in step 10.
13: N-Boc-serine-benzyl ether
14: As in step 7.
15: As in step 5
16: D:o as in step 4
17: N-Boc-asparagine-xanthydryl derivative
18: As in step 4
19: N-Boc-aspartic acid $\beta$-benzyl ester
20: As in step 5
21: N-Boc-isoleucine
22: As in step 4
23: As in step 7
24: As in step 10
25: N-Boc-glycine
26: As in step 5
27: As in Step 2
28: As in step 10
29: As in step 4
30: As in step 19

The protecting groups are removed from the protected resin-bond peptide, the resin is cleaved off using anhydrous hydrogen fluoride at 0° C. for 30 minutes, and the peptide is extracted from the resin using a 10% by weight aqueous solution of acetic acid. After evaporation the residue is purified by gel filtration on Sephadex G 25 Fine in 0.1 M $NH_4HCO_3$. AFter lyophilization of the peptide a satisfactory amino acid analysis is obtained, together with a molecular weight of approximately 3300, as determined by gel filtration. The theoretical MW value is 3320.80.

The polypeptide prepared according to the foregoing was investigated with regard to its ability to inhibit the hemagglutination reaction between tanned red sheep blood cells labelled with natural cancer antigen and antibodies prepared by using natural cancer antigen (CAPA or TPA). For details concerning this technique reference can be made to the above-identified Swedish patent application 73-08917-9 and U.S. Pat. No. 3,960,827. The specific activity of the polypeptide was found to be about 0.2 Units per milligram (U/mg). Said Unit for specific activity is defined as 1/6 of the quantity of active polypeptide required to label $10^9$ sheep blood cells so as to be fully agglutinated by a minimum number or amount of antibodies (maximum dilution of antibodies).

For the purpose of investigating which functions are critical for the activity of the polypeptide, the basic structure of which is given above, certain experiments were carried out. The arginines were thus blocked with cyclohexanedione at pH 13 resulting in almost complete loss of activity. If, however, the polypeptide is subjected only to a basic environment, wherein the pH is 13 for the same period of time, only a minor part of the activity is lost. This indicates the fact that the arginine presence in the polypeptide according to the present invention is of decisive importance for the antigenic activity.

From the character of the structure, it is clear that the polypeptide has an acidic character, thus being negatively charged in a neutral solution while, however, maintaining the positive charge of the arginine part thereof.

The chemical basis for the antigenic character of the polypeptide has thus been set forth in the foregoing description. The remarkable specific activity which has been obtained by means of a synthetically prepared product, the activity of which can be said to be of a haptenic nature, due to the small determinant group, constitutes a pioneering advance with regard to the application of immunology and testing, i.e. diagnosis, within the cancer area.

Clearly and in accordance with what is known in immunology, antigenic activity is a function not only of the structure of the haptenic determinant group, but also of the size of the polypeptide. Said size does not, however, effect the specificity of the peptide but only the degree of activity, inasmuch as a larger molecule tends to be more active than a smaller one. Therefore, an improved activity is obtained if the polypeptide is arranged on a suitable immunogenically active carrier, for instance a protein, such as albumin, for instance egg white. Already the polypeptide in its basic structural form, i.e., having at least twenty (20) amino acid units, does, however, show an antigenic activity which is sufficient to enable the polypeptide to react with corresponding antibodies.

In Example 1 as described above the antigenic activity of the synthesized polypeptide is determined in the following manner.

For quantitative determination of the amount of polypeptide 7 mgs of the peptide are dissolved in 1.4 mls of buffer grade serum, i.e. a physiological saline solution containing 2% of inert human serum and buffered to a pH of about 7.5 with a phosphate buffer. Under serial dilution a series of samples of said solution having a decreasing polypeptide concentration is prepared and to each of said samples there is added a pre-determined amount of anti-serum containing antibodies specific to TPA. To each of the resulting samples there is then added, after incubation, a predetermined amount of the polypeptide carried on a particulate carrier, hemagglutination taking place to an extent corresponding to the amount of available antibodies. In parallel there is prepared a corresponding series of control samples containing known decreasing amounts of TPA. The diameters of the hemagglutination depositions of the control samples are then visually compared with those of the control samples to estimate activity.

EXAMPLE 2

In the same manner as given in Example 1 the following polypeptide is prepared and found to be about equally immunologically active as the polypeptide of Example 1:

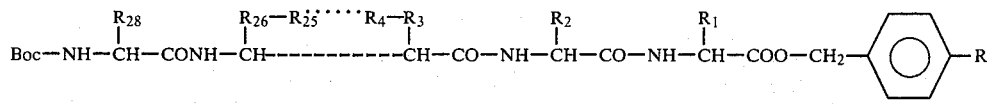

wherein: R denotes the resin; Boc is a t-butyloxy carbonyl group;

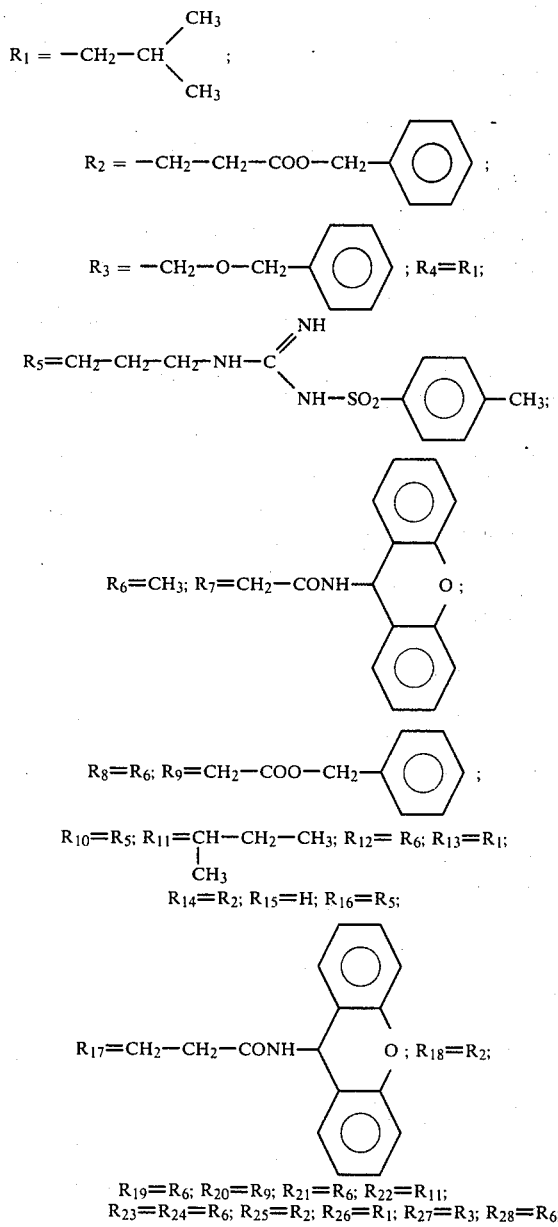

The amino acid sequence between the t-butyloxycarbonyl group and the resin part may be expressed in the following manner using the foregoing abbreviations regarding the amino acids: (II) -Ala-Ser-Leu-Glu-Ala-Ala-Ile-Ala-Asp-Ala-Glu-Gln-Arg-Gly-Glu-Leu-Ala-Ile-Arg-Asp-Ala-Asn-Ala-Arg-Leu-Ser-Glu-Leu-.

0.4 mmole of Boc-leucine (resinbenzyl ester) was transferred to the cuvette of a Beckman peptide synthesizer and swollen in methylene chloride ($CH_2Cl_2$). The protecting Boc-group was removed by treatment with trifluoroacetic acid in excess in methylene chloride. After washing with methylene chloride the resin was neutralized with triethylamine and again washed with methylene chloride. N-Boc-glutamic acid benzyl ester (coupling step 1) and cyclohexylcarbodiimide was added dissolved in $CH_2Cl_2$, and the mixture was stirred for 30 minutes. The resin was washed and the coupling step repeated. This terminates the introduction of $R_2$ in step 1 according to the above.

Step 2 of the synthesis starts by removal of an N-Boc from the N-terminated amino acid and repetition of the coupling step while using another N-Boc-amino acid. To build up the above amino acid sequence the following reagents are used in the subsequent steps:
in
step 2: N-Boc-glutamic acid γ-benzylester
3: N-Boc-serine-benzyl ether
4: N-Boc-leucine
5: N-Boc-G-tosylarginine
6: N-Boc-alanine
7: N-Boc-asparagine-xanthydryl derivative
8: D:o as in step 6
9: N-Boc-aspartic acid β-benzyl ester
10: D:o as in step 5
11: N-Boc-isoleucine
12: D:o as in step 6
13: D:o as in step 4
14: D:o as in step 2
15: N-Boc-glycine
16: D:o as in step 5
17: N-Boc-glutamine-xanthydryl derivative
18: D:o as in step 2
19: D:o as in step 6
20: D:o as in step 9
21: D:o as in step 6
22: D:o as in step 11
23: D:o as in step 6
24: D:o as in step 6
25: D:o as in step 2
26: D:o as in step 4
27: D:o as in step 3
28: D:o as in step 6

The resulting protected resin-bond peptide is then treated and analyzed in accordance with the procedure of Example 1.

The molecular weight as determined by gel filtration is approximately 3000, whereas the theoretical molecular weight is 2936.38.

The results of amino acid analyses made on the polypeptides of examples 1 and 2 above are summarized in the table below. The figures given therein refer to mole percent of each amino acid, i.e. the numbers of the respective amino acids per 100 amino acids of the peptide. The figures given in the table correspond satisfactorily to the theoretical values.

TABLE

| Ex. No. | Asp | Ser | Glu | Gly | Ala | Ile | Leu | Lys | Arg |
|---|---|---|---|---|---|---|---|---|---|
| 1 | 6.99 | 4.11 | 20.94 | 2.53 | 26.61 | 3.28 | 16.87 | 5.39 | 13.27 |
| 2 | 10.45 | 7.03 | 17.09 | 2.75 | 30.43 | 6.74 | 15.48 | — | 10.02 |

The present invention is in no way limited to the foregoing specific embodiments. Thus, in preparing the polypeptide, the resin may be any material containing benzene rings and in addition at least one group having the ability of binding N-protected amino acids by esterification. The ester bond must be relatively easy to hydrolyse and, of course, must be easier to cleave than the peptide bonds in the polypeptide. However, the ester bond must be sufficiently stable to be able to withstand the reaction conditions under the synthesis.

As an alternative to the above mentioned coupling reagent, dicyclohexyl carbodiimide, when attaching glutamine and asparagine units, coupling may instead be carried out with so-called active esters, for instance cyanomethyl, thiophenyl or nitrophenyl esters. As a solvent in the synthesis so-called aprotic solvents are suitable, particularly solvents that are somewhat hydrophilic or "semipolar".

Regarding useful groups to protect the N-amino acids, it is noted that t-butyloxy carbonyl groups, wherein one or two methyl groups are replaced by phenyl, also may be advantageously used. In this connection it can be mentioned that the product obtained in the synthesis is provided with N-protecting groups and attached to a resin by esterification, and that it advantageously can be stored for a long period of time without being destroyed. In connection with the use of the polypeptide, the protecting groups and the resin part may then be removed.

In the amino acid sequences given in the present preparation, the terminal groups (after removal of the protecting groups and the resin part) are always amino group and carboxyl group, respectively. The amino group is found at the left end of the chain, whereas the carboxyl group is found at the opposite end of the amino acid sequence.

I claim:

1. A synthetic antigenically active polypeptide, which includes the amino acid sequence: H-Asp-Ala-Glu-Gln-Arg-Gly-Glu-Leu-Ala-Ile-ARg-Asp-Ala-Asn-Ala-Arg-Leu-Ser-Glu-Leu-OH.

2. A polypeptide according to claim 1, which includes the amino acid sequence: H-Asp-Ala-Glu-Gln-Arg-Gly-Glu-Leu-Ala-Ile-Arg-Asp-Ala-Asn-Ala-Arg-leu-Ser-Glu-Leu-Glu-Ala-Ala-Leu-Gln-Arg-Ala-Lys-Gln-Asp-OH.

3. A polypeptide according to claim 1, which includes the amino acid sequence: H-Ala-Ser-Leu-Glu-Ala-Ala-Ile-Ala-Asp-Ala-Glu-Gln-Arg-Gly-Glu-Leu-Ala-Ile-Arg-Asp-Ala-Asn-Ala-Arg-Leu-Ser-Glu-Leu-OH.

4. An antigenic agent useful for diagnostic purposes, comprising a polypeptide as claimed in claim 1 covalently bonded to an immunogenically active carrier.

5. An agent according to claim 4, wherein the carrier is a protein.

6. An agent according to claim 4, wherein the carrier is an albumin.

7. A antigenic composition comprising a polypeptide as claimed in claim 1 or an antigenic agent as claimed in claim 4 together with a diagnostically acceptable carrier or diluent.

8. A method for detemining the presence or absence in a biological sample of antibodies monospecific to a polypeptide according to claim 1 which comprises introducing into the sample a polypeptide as claimed in claim 1 or an agent as claimed in claim 4 or a composition as claimed in claim 7 and determining the presence or absence of agglutination.

* * * * *

UNITED STATES PATENT AND TRADEMARK OFFICE
CERTIFICATE OF CORRECTION

PATENT NO. : 4,327,075
DATED : April 27, 1982
INVENTOR(S) : Björn Lüning

It is certified that error appears in the above—identified patent and that said Letters Patent is hereby corrected as shown below:

[57] ABSTRACT, line 6; "convalently" should read -- covalently --
Col. 5, line 51; "AFter" should read -- After --
Col. 10, line 8; "-ARg-" should read -- -Arg- --
Col. 10, line 13; "leu-" should read -- Leu- --

Signed and Sealed this

Third Day of August 1982

[SEAL]

Attest:

GERALD J. MOSSINGHOFF

Attesting Officer    Commissioner of Patents and Trademarks